US012742769B2

(12) United States Patent
Azmi et al.

(10) Patent No.: US 12,742,769 B2
(45) Date of Patent: Sep. 22, 2026

(54) SYSTEMS AND METHODS FOR DETERMINING OIL QUALITY BASED ON PUMP CURVE DATA

(71) Applicant: SAUDI ARABIAN OIL COMPANY, Dhahran (SA)

(72) Inventors: Mutlaq F. Azmi, As Saffaniyah (SA); Naif M. Alghuthayf, Dammam (SA); Mohammed A. Alswayied, Riyadh (SA); Basil S. Abuhadi, Jeddah (SA); Fawaz S. Alshammari, Al Ahmadi (KW)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 370 days.

(21) Appl. No.: 18/505,991

(22) Filed: Nov. 9, 2023

(65) Prior Publication Data

US 2025/0155423 A1 May 15, 2025

(51) Int. Cl.
*G01N 33/28* (2006.01)
*F04B 49/06* (2006.01)

(52) U.S. Cl.
CPC ........ *G01N 33/2823* (2013.01); *F04B 49/065* (2013.01)

(58) Field of Classification Search
CPC ........ G01N 33/2823; G01N 9/32; G01N 9/26; F04B 49/065; G01F 1/88; G01F 15/005;
(Continued)

(56) References Cited

U.S. PATENT DOCUMENTS 3,453,868 A * 7/1969 Williams, Jr. ..... G01N 33/2823 73/32 R
4,890,480 A 1/1990 Young
(Continued)

FOREIGN PATENT DOCUMENTS

JP S5888636 A 5/1983
WO 2016043866 A1 3/2016
WO 2020244684 A1 12/2020

OTHER PUBLICATIONS

Noor Syaffynas bt Yusoff, Noor Syaffynas. "Centrifugal Pump Characteristics for Crude Oil Transfer." (2010). (Year: 2010).*
(Continued)

*Primary Examiner* — Timothy P Graves
(74) *Attorney, Agent, or Firm* — Osha Bergman Watanabe & Burton LLP

(57) ABSTRACT

Various systems, methods, and devise are discussed. As an example, systems are discussed that include: a first pressure sensor deployed upstream from a pump and configured to sense a first pressure of an uncompressible liquid moving in a first pipe toward the pump, a second pressure sensor deployed downstream from the pump and configured to sense a second pressure of the uncompressible liquid moving in a second pipe away from the pump, and a quality determination device. The quality determination device is configured to: receive the first pressure from the first pressure sensor, receive the second pressure from the second pressure sensor, determine in real-time an uncompressible liquid quality value based at least in part on the first pressure, the second pressure, and a pump data from a pump curve of the pump.

19 Claims, 9 Drawing Sheets

(58) Field of Classification Search
CPC ... G01F 1/363; G01F 1/36; G01F 1/74; G01F 15/02; F04D 15/0088
See application file for complete search history.

(56) References Cited

U.S. PATENT DOCUMENTS

| | | | | |
|---|---|---|---|---|
| 5,400,657 | A | 3/1995 | Kolpak et al. | |
| 6,357,536 | B1 | 3/2002 | Schrader et al. | |
| 7,366,621 | B2 | 4/2008 | Sprague | |
| 7,668,688 | B2 | 2/2010 | Najim Al-Khamis | |
| 7,860,669 | B2 | 12/2010 | Najim Al-Khamis | |
| 9,952,078 | B2 | 4/2018 | Ding et al. | |
| 2003/0089161 | A1 | 5/2003 | Gysling | |
| 2005/0191184 | A1 | 9/2005 | Vinson, Jr. | |
| 2013/0204546 | A1 | 8/2013 | Devine et al. | |
| 2017/0183215 | A1 | 6/2017 | Ayers et al. | |
| 2017/0211505 | A1 | 7/2017 | Anderson et al. | |
| 2020/0018739 | A1* | 1/2020 | Khan | E21B 49/081 |

OTHER PUBLICATIONS

International Search Report issued for corresponding international patent application No. PCT/US2024/053527, mailed Feb. 26, 2025 (6 pages).

Written Opinion issued for corresponding international patent application No. PCT/US2024/053527, mailed Feb. 26, 2025 (10 pages).

Syaffynas BT Yusoff, Noor, "Centrifugal Pump Characteristics for Crude Oil Transfer"; A dissertation submitted to the Mechanical Engineering Programme Universiti Teknologi Petronas in partial fulfulment of the requirements for the degree of Bachelor of Enginnering; pp. 1-78; Jan. 2010 (78 pages).

* cited by examiner

SYSTEMS AND METHODS FOR DETERMINING OIL QUALITY BASED ON PUMP CURVE DATA

BACKGROUND

Quality is a key component in the market price of crude oil. In some cases, different crude oil types, each with different qualities, are mixed together to yield a crude oil mixture that meets a desired quality. To make this possible, the quality of each of a number of types of crude oil must be established, and then an appropriate mixture determined. In a typical scenario, samples of different types of crude oil are taken to a laboratory where they are analyzed using complex analyzers to assign a quality to each of the types of crude oil. This process of analyzing crude oil quality is both complex and time consuming.

Hence, there exists a need in the art for advanced systems and methods for determining quality of crude oil.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In general, in one aspect, embodiments relate to systems that include: a first pressure sensor deployed upstream from a pump and configured to sense a first pressure of an uncompressible liquid moving in a first pipe toward the pump, a second pressure sensor deployed downstream from the pump and configured to sense a second pressure of the uncompressible liquid moving in a second pipe away from the pump, and a quality determination device. The quality determination device is configured to: receive the first pressure from the first pressure sensor, receive the second pressure from the second pressure sensor, determine in real-time an uncompressible liquid quality value based at least in part on the first pressure, the second pressure, and a pump data from a pump curve of the pump.

In general, in one aspect, embodiments relate to methods for real-time oil quality determination. Such methods include: receiving by a processing resource from a first pressure sensor via a first communication link, a first real-time pressure of oil moving in a first pipe toward a pump inlet of a pump; receiving by the processing resource from a second pressure sensor via a second communication link, a second real-time pressure of the oil moving in a second pipe away from a pump outlet of the pump; receiving by the processing resource from a temperature sensor via a third communication link, a real-time temperature of the oil; receiving by the processing resource from a flow sensor via a fourth communication link, a flow of the oil; and determining in real-time, by the processing resource, an oil quality value based at least in part on the first real-time pressure, the second real-time pressure, the real-time temperature, the real-time flow, and a pump data from a pump curve of the pump Other aspects and advantages of the claimed subject matter will be apparent from the following description and the appended claims.

BRIEF DESCRIPTION OF DRAWINGS

Specific embodiments of the disclosed technology will now be described in detail with reference to the accompanying figures. Like elements in the various figures are denoted by like reference numerals for consistency. In some instances, a sub-label consisting of a lower-case letter is associated with a reference numeral to denote one of multiple similar components. When reference is made to a reference numeral without specifying an existing sub-label, it is intended to refer to all such multiple similar components.

DETAILED DESCRIPTION

Figure 1:
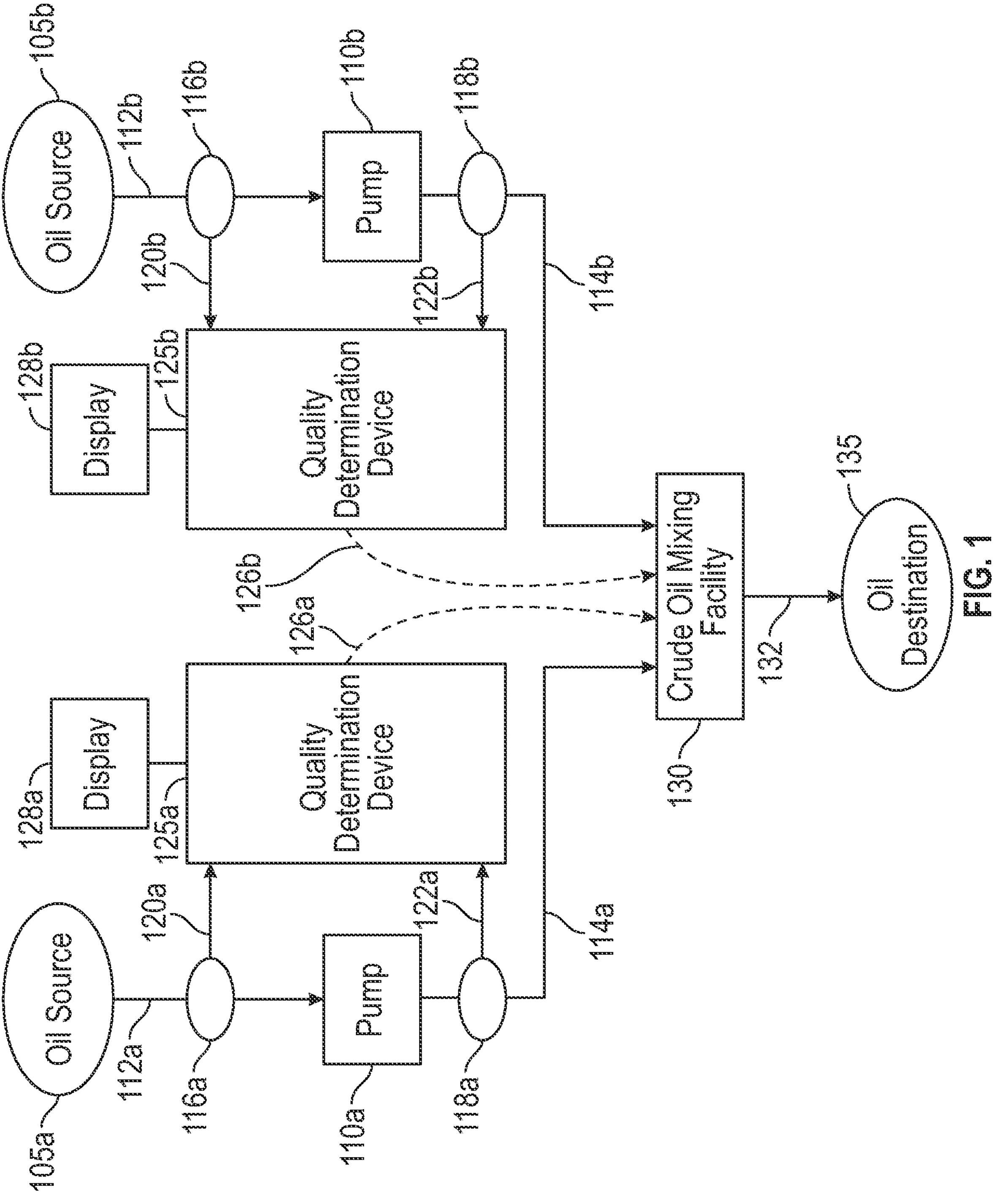
FIG. 1 illustrates a plurality of quality determination devices each transmitting an uncompressible liquid quality value to an oil mixing facility in accordance with some embodiments.

Various embodiments of the disclosure will now be described in detail with reference to the accompanying figures. Like elements in the various figures are denoted by like reference numerals for consistency.

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as using the terms “before”, “after”, “single”, and other such terminology. Rather, the use of ordinal numbers is to distinguish between the elements. By way of an example, a first element is distinct from a second element, and the first element may encompass more than one element and succeed (or precede) the second element in an ordering of elements.

It is to be understood that the singular forms "a," "an," and "the" include plural referents unless the context clearly dictates otherwise. Thus, for example, reference to "cell" includes reference to one or more of such cells.

Terms such as "approximately," "substantially," etc., mean that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

It is to be understood that one or more of the elements shown in the flowchart may be omitted, repeated, and/or performed in a different order than the order shown. Accordingly, the scope disclosed herein should not be considered limited to the specific arrangement of steps shown in the flowchart.

Although multiple dependent claims are not introduced, it would be apparent to one of ordinary skill that the subject matter of the dependent claims of one or more embodiments may be combined with other dependent claims.

As used herein, the phrase "uncompressible liquid quality value" is used in its broadest sense to mean any value representing the quality of an uncompressible liquid. Thus, as some example, a specific gravity of an uncompressible liquid may be an uncompressible liquid quality value. As another example, a temperature corrected specific gravity of an uncompressible liquid may be an uncompressible liquid quality value.

In the following description of FIGS. 1-9, any component described with regard to a figure, in various embodiments disclosed herein, may be equivalent to one or more like-named components described with regard to any other figure. For brevity, descriptions of these components will not be repeated with regard to each figure. Thus, each and every embodiment of the components of each figure is incorporated by reference and assumed to be optionally present within every other figure having one or more like-named components. Additionally, in accordance with various embodiments disclosed herein, any description of the components of a figure is to be interpreted as an optional embodiment which may be implemented in addition to, in conjunction with, or in place of the embodiments described with regard to a corresponding like-named component in any other figure.

Various embodiments of uncompressible liquid quality determination systems are disclosed. The systems may be configured to receive real-time measurements of an uncompressible liquid moving through a pump. These measurements may be used along with known characteristics of the pump to determine an uncompressible liquid quality value. This uncompressible liquid quality value may be: (a) updated as the system continues operating, (b) displayed locally, and/or (c) transmitted to a recipient device or system. This recipient device or system may be integrated with, for example, an oil mixing facility that may be configured to use uncompressible liquid quality values from a number of uncompressible liquid quality determination systems to select volumes of oil from different oil sources for mixing to yield a mixed product of a desired quality. The uncompressible liquid may be, but is not limited to, crude oil.

Turning to FIG. 1, a plurality of quality determination devices 125 each transmitting an uncompressible liquid quality value 126 (e.g., a quality determination device 125*a* transmitting uncompressible liquid quality value 126*a* and a quality determination device 125*b* transmitting uncompressible liquid quality value 126*b*) to an oil mixing facility 130 is shown in accordance with some embodiments. Quality determination device 125 may transmit uncompressible liquid quality value 126 using any transmission medium known in the art including, but not limited to, wired and wireless communication links. Further, quality determination device 125 may transmit uncompressible liquid quality value 126 using any transmission protocol known in the art.

In addition, each of quality determination devices 125 display uncompressible liquid quality value 126 via a local display 128 (e.g., a display 128*a* and a display 128*b*). Display 128 may be any device known in the art capable of displaying an uncompressible liquid quality value. In some cases, display 128 may be integrated with quality determination device 125 or may be a separate display mounted local to quality determination device 125.

Quality determination device 125 receives real-time measurements 120 (e.g., real-time measurements 120*a* and real-time measurements 120*b*) of oil moving from an oil source (e.g., an oil source 105*a* and an oil source 105*b*) toward an oil pump (e.g., a pump 110*a* and a pump 110*b*). In some embodiments, pump 110 is a crude oil centrifugal pump. Based upon the disclosure provided herein, one of ordinary skill in the art will recognize a variety of pumps that may be used in relation to different embodiments. Real time measurements 120 are provided by a sensor set 116 (e.g., a sensor set 116*a* and a sensor set 116*b*) located upstream from pump 110. Sensor set 116 includes at least one pressure sensor.

Quality determination device 125 additionally receives real-time measurements 122 (e.g., real-time measurements 122*a* and real-time measurements 122*b*) of oil moving from pump 110 toward crude oil mixing facility 130 via a pipe 114 (e.g., a pipe 114*a* and a pipe 114*b*). Real time measurements 122 are provided by a sensor set 118 (e.g., a sensor set 118*a* and a sensor set 118*b*) located downstream from pump 110. Sensor set 118 includes at least one pressure sensor.

Quality determination device 125 determines uncompressible liquid quality value 126 using real-time measurements 120, real-time measurements 122, and a known characteristic of pump 110. A pump curve for pump 110 may be maintained in a memory of quality determination device 125. This pump curve may be accessed using one or more of real-time measurements 120 or real-time measurements 122 to obtain the known characteristic of pump 110. In some embodiments, the known characteristic of pump 110 may be accessed from a table of values representing the pump curve for pump 110. This table of values may be maintained in a memory of quality determination device 125. In some embodiments, one of real-time measurements 120 or real-time measurements 122 includes a measured flow of uncompressible liquid moving through pipes 112, 114. In such embodiments, the known characteristic of pump 110 may be head to flowrate and may be accessed from the table of values using the measured flow.

Crude oil mixing facility 130 receives oil from different oil sources 105 via a number of pipes 114 and uncompressible liquid quality values 126 each transmitted from a respective quality determination device 125. Oil sources 105 may be any source of oil including, but not limited to, a producing well or a storage tank. Based upon the disclosure provided herein, one of ordinary skill in the art will recognize a number of oil sources that may be used in relation to different embodiments.

Crude oil mixing facility 130 may use the uncompressible liquid quality values 126 to select different volumes of oil from each of oil sources 105 to create a mixed product 132 that exhibits a desired quality. Mixed product 132 is provided to an oil destination 135. Oil destination 135 may be any destination for oil including, but not limited to, a tank or an oil distribution pipeline. Based upon the disclosure provided herein, one of ordinary skill in the art will recognize a number of oil destinations that may be used in relation to different embodiments. While FIG. 1 shows oil being mixed from two oil sources 105, in different embodiments oil may be mixed from more than two sources. Any mixing facility or mixing process known in the art modifiable to use uncompressible liquid quality values may be used in relation to different embodiments.

Figure 2A:
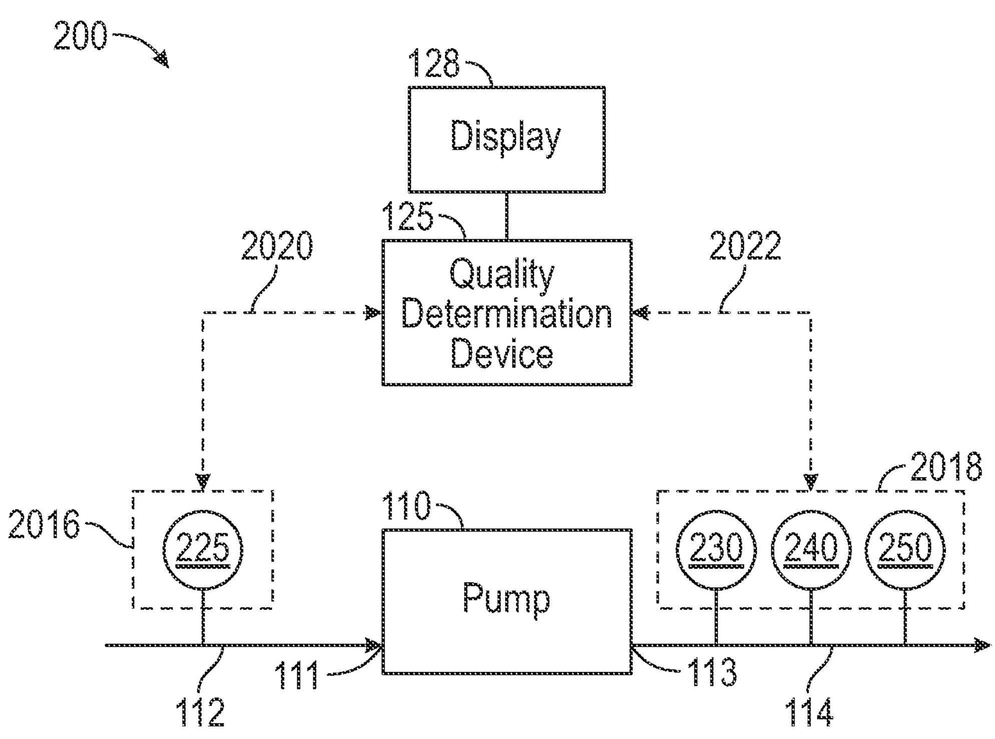
FIGS. 2A-2B show uncompressible liquid quality determination systems in accordance with various embodiments.

Turning to FIG. 2A, an uncompressible liquid quality determination system 200 is shown in accordance with various embodiments. Uncompressible liquid quality determination system 200 is configured for use in relation to pump 110 that is fixed at a particular location, and not part of the system. Uncompressible liquid quality determination system 200 includes: a sensor set 2016 measuring uncompressible liquid moving in pipe 112 toward a pump inlet 111 of pump 110, and a sensor set 2018 measuring uncompressible liquid moving in pipe 114 away from a pump outlet 113 of pump 110. As shown, sensor set 2016 includes a pressure sensor 225 measuring a suction pressure ($P_s$). Pressure sensor 225 may be any pressure sensor known in the art that is capable of measuring the suction pressure of pump 110. Further, pressure sensor 225 is located sufficiently close to pump inlet 111 to provide an accurate measurement of the suction pressure.

Sensor set 2018 includes: a pressure sensor 230 measuring a discharge pressure ($P_d$), a temperature sensor 240 measuring a temperature (T) of the uncompressible liquid, and a flow sensor 250 measuring a flow (F) of the uncompressible liquid. Pressure sensor 230 may be any pressure sensor known in the art that is capable of measuring the discharge pressure of pump 110. Further, pressure sensor 230 is located sufficiently close to pump outlet 113 to provide an accurate measurement of the discharge pressure. Temperature sensor 240 may be any temperature sensor known in the art that is capable of measuring the temperature of an uncompressible liquid flowing in a pipe. Flow sensor 250 may be any temperature sensor known in the art that is capable of measuring the flow of an uncompressible liquid flowing in a pipe. Temperature sensor 240 and flow sensor 250 are located sufficiently close to pump 110 to provide an accurate measurement of the temperature and flow of the uncompressible liquid at the pump.

Sensor set 2016 transmits the suction pressure to quality determination device 125 via a communication link 2020. Communication link 2020 may be any communication link known in the art including, but not limited to, a wired communication link or a wireless communication link. Further, the suction pressure may be transmitted from sensor set 2016 using any communication protocol known in the art.

Sensor set 2018 transmits the discharge pressure, the temperature of the uncompressible liquid, and the flow of the uncompressible liquid via a communication link 2022. In some embodiments, communication link 2022 may include a communication link dedicated to each of the discharge pressure, the temperature, and the flow, respectively. In other embodiments, communication link 2022 may include a single communication link that handles transmission of the discharge pressure, the temperature, and the flow. Communication link 2022 may be any communication link known in the art including, but not limited to, a wired communication link or a wireless communication link. Further, each of the discharge pressure, the temperature, and the flow may be transmitted from sensor set 2018 using any communication protocol known in the art.

In operation, quality determination device 125 receives the suction pressure from pressure sensor 225, the discharge pressure from pressure sensor 230, the temperature from temperature sensor 240, and the flow from flow sensor 250 in real-time. Such real-time data may be received immediately as the respective sensor indicates a change or within a known update rate for the particular sensor. In either case, the data is considered real-time data. Quality determination device 125 accesses a head to flowrate (H) value from a table of values representing a pump curve of pump 110 using the received flow.

Quality determination device 125 calculates a specific gravity (SG) of the uncompressible liquid in accordance with the following equation:

$$SG=(P_d-P_s)*2.31/H.$$

In some embodiment, quality determination device 125 calculates a temperature corrected specific gravity ($SG_{60}$) for a temperature of sixty (60) degrees Fahrenheit using the following equation:

$$SG_{60}=SG+[3.31*10^{-4}*(T(°\ F.)-60)].$$

The temperature corrected specific gravity can be converted to American Petroleum Institute (API) gravity using the following equation:

$$\text{API Gravity}=(141.5/SG_{60})-131.5.$$

In the case of crude oil production, the calculated API gravity can be seen by a local operator on display 128 and used to compare with American Petroleum Institute (API) specifications. The comparison provides an onsite, real-time indication to the local operator as to the quality of the oil being produced and if the production is within a desired API range.

Figure 2B:
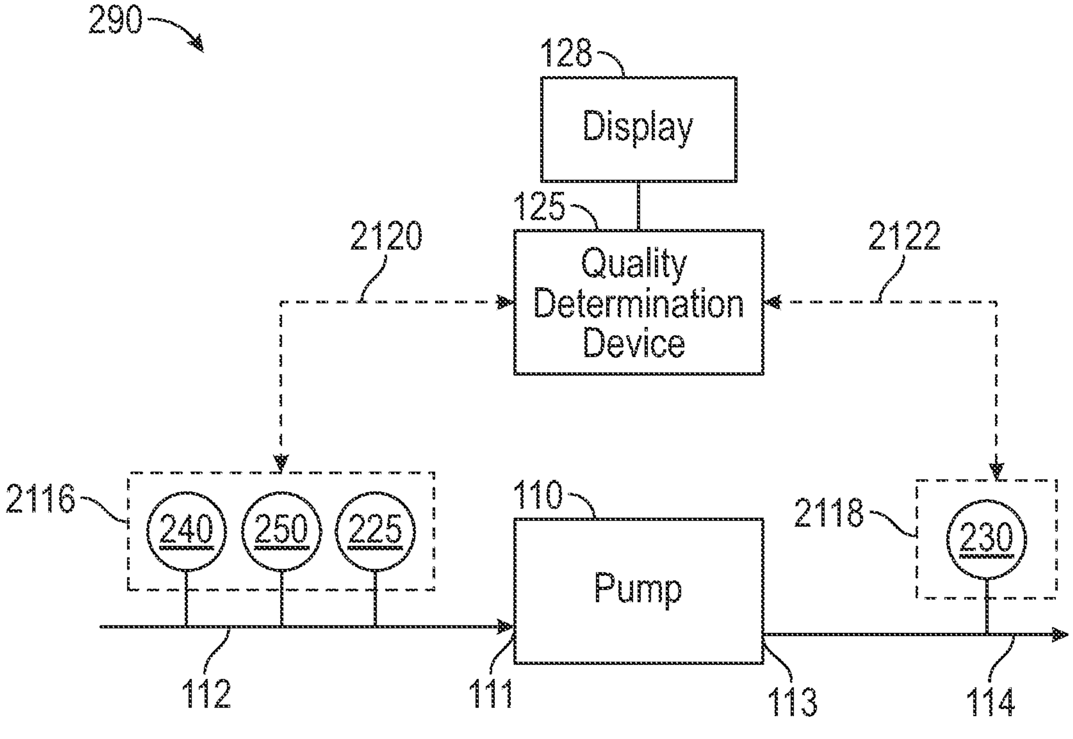

Turning to FIG. 2B, another uncompressible liquid quality determination system 290 is shown in accordance with other embodiments. Similar to uncompressible liquid quality determination system 200 discussed above in relation to FIG. 2A, uncompressible liquid quality determination system 290 is configured for use in relation to a pump that is fixed at a particular location. Uncompressible liquid quality determination system 290 includes: a sensor set 2116 measuring uncompressible liquid moving in pipe 112 toward pump inlet 111 of pump 110, and a sensor set 2118 measuring uncompressible liquid moving in pipe 114 away from pump outlet 113 of pump 110. As shown, sensor set 2116 includes: a pressure sensor 225 measuring a suction pressure ($P_s$), a temperature sensor 240 measuring a temperature (T) of the uncompressible liquid, and a flow sensor 250 measuring a flow (F) of the uncompressible liquid. Sensor set 2118 includes a pressure sensor 230 measuring a discharge pressure ($P_d$). Sensor set 2116 and sensor set 2118 are installed at the location near pump 110. Operation of uncompressible liquid quality determination system 290 is similar to that described above in relation to uncompressible liquid quality determination system 200.

Sensor set 2116 transmits the suction pressure, the temperature of the uncompressible liquid, and the flow of the uncompressible liquid via a communication link 2120. In some embodiments, communication link 2120 may include a communication link dedicated to each of the suction pressure, the temperature, and the flow, respectively. In other embodiments, communication link 2120 may include a single communication link that handles transmission of the suction pressure, the temperature, and the flow. Communication link 2120 may be any communication link known in the art including, but not limited to, a wired communication link or a wireless communication link. Further, each of the discharge pressure, the temperature, and the flow may be transmitted from sensor set 2116 using any communication protocol known in the art.

Sensor set 2118 transmits the discharge pressure to quality determination device 125 via a communication link 2122. Communication link 2122 may be any communication link known in the art including, but not limited to, a wired communication link or a wireless communication link. Further, the suction pressure may be transmitted from sensor set 2118 using any communication protocol known in the art.

Figure 3:
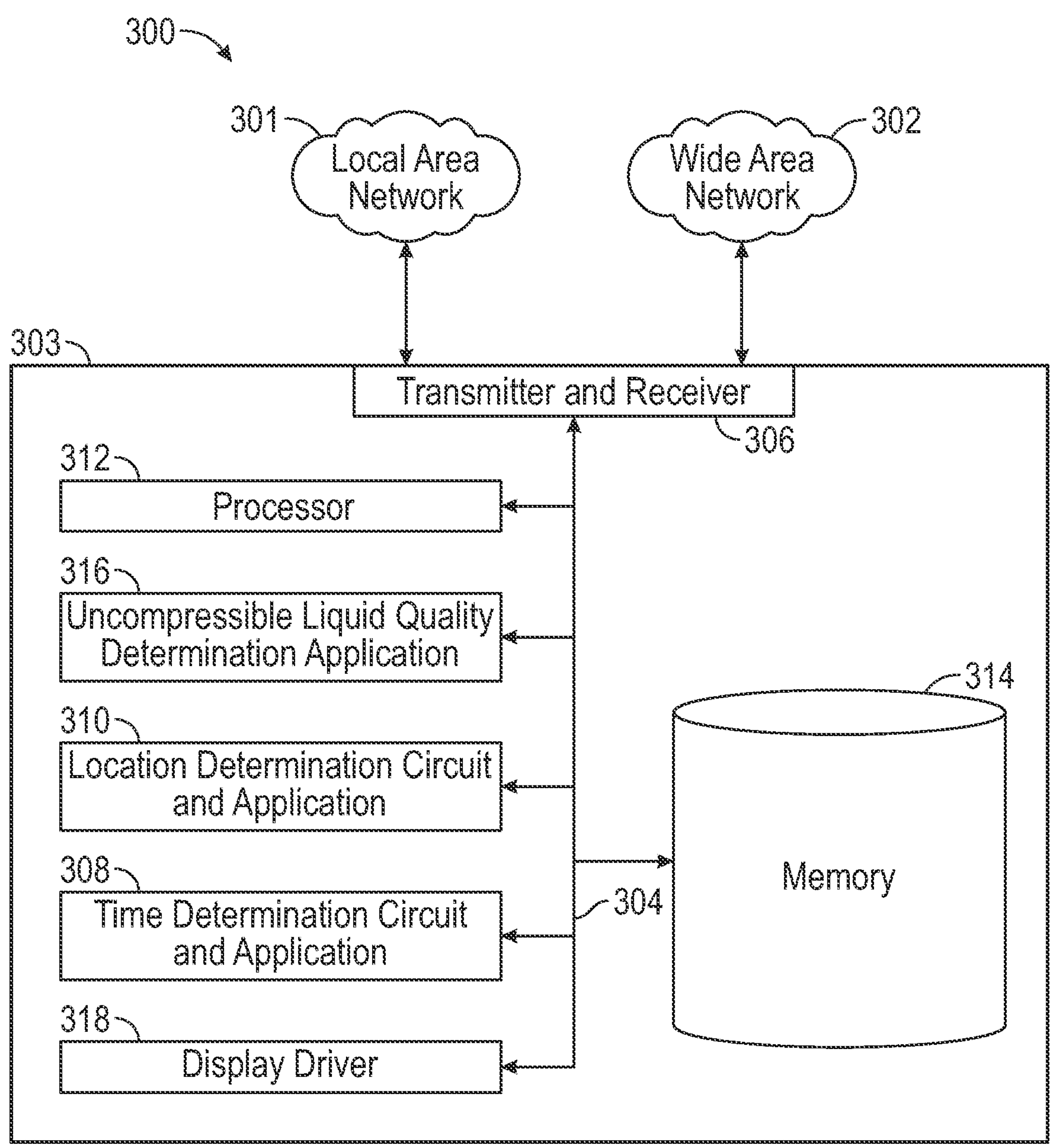
FIG. 3 shows a computer system in accordance with one or more embodiments.

Embodiments of quality determination device 125 may be implemented on a computer system. Turning to FIG. 3, a block diagram 300 is provided for a computer system 303, a local area network 301, and a wide area network 302 that may be used to provide computational functionalities and communications associated with described algorithms, methods, functions, processes, flows, and procedures as described in the instant disclosure, according to an implementation. Computer system 303 is one example of a large number of computer systems that may be used to implement different embodiments. Based upon the disclosure provided herein, one of ordinary skill in the art will recognize a wide variety of computer systems that may be used in relation to different embodiments.

Computer system 303 includes a transmitter and receiver 306 configured to transmit information to a recipient device via wide area network 302 and receive information via local area network 301. In some embodiments, transmitter and receiver 306 receives sensor data via local area network 301 and transmits an uncompressible liquid quality value to a recipient device via wide area network 302. The sensor data may include, but is not limited to, suction pressure, discharge pressure, temperature, and flow. Local area network 301 may be any network known in the art for communicably coupling computer system 303 to transceivers located local to computer system 303, and wide area network 302 may be any network known in the art for communicably coupling computer system 303 to transceivers located a relatively large distance from computer system 303. Based upon the disclosure provided herein, one of ordinary skill in the art will recognize a variety of wired networks and wireless networks, and communication protocols that may be used to implement local area network 301 and wide area network 302.

Generally, transmitter and receiver 306 includes logic encoded in software or hardware (or a combination of software and hardware) and operable to communicate with local area network 301 and wide area network 302. More specifically, transmitter and receiver 306 may include software supporting one or more communication protocols associated with communications such that the network or interface's hardware is operable to communicate physical signals within and outside of the illustrated computer system 303.

While computer system 303 is shown as including only transmitter and receiver 306, other interfaces may be included according to particular needs, desires, or particular implementations of computer system 303. For example, computer system 303 may include a USB interface or a serial port. Based upon the disclosure provided herein, one of ordinary skill in the art will recognize a variety of interfaces that may be included in computer system 303.

Computer system 303 is intended to encompass any computing device such as a high-performance computing (HPC) device, a server, desktop computer, laptop/notebook computer, wireless data port, smart phone, personal data assistant (PDA), tablet computing device, one or more processors within these devices, or any other suitable processing device, including both physical or virtual instances (or both) of the computing device. Additionally, computer system 303 may include a computer that includes an input device, such as a keypad, keyboard, touch screen, or other device that can accept user information, and an output device that conveys information associated with the operation of computer system 303, including digital data, visual, or audio information (or a combination of information), or a graphical user interface (GUI).

Computer system 303 can serve in a role as a client, network component, a server, a database or other persistency, or any other component (or a combination of roles) of a computer system for performing the subject matter described in the instant disclosure. In some implementations, one or more components of computer system 303 may be configured to operate within environments, including cloud-computing-based, local, global, or other environment (or a combination of environments).

At a high level, computer system 303 is an electronic computing device operable to receive, transmit, process, store, or manage data and information associated with the described subject matter. According to some implementations, computer system 303 may also include or be communicably coupled with an application server, e-mail server, web server, caching server, streaming data server, business intelligence (BI) server, or other server (or a combination of servers).

Computer system 303 can receive requests over either local network 301 or wide area network 302 from a client application (for example, executing on another computer system (not shown) and responding to the received requests by processing the said requests in an appropriate software application. In addition, requests may also be sent to computer system 303 from internal users (for example, from a command console or by other appropriate access method), external or third-parties, other automated applications, as well as any other appropriate entities, individuals, systems, or computers.

Each of the components of computer system 303 can communicate using a system bus 304. The components may include, but are not limited to, one or more computer processors 312, an uncompressible liquid quality determination application 316, a location determination circuit and application 310, a time determination circuit and application 308, and a display driver 318. Although illustrated as a single computer processor 312 in FIG. 3, two or more processors may be used according to particular needs, desires, or particular implementations of computer system 303. Generally, the computer processor 312 executes instructions and manipulates data to perform the operations of computer system 303 and any algorithms, methods, functions, processes, flows, and procedures as described in the instant disclosure.

Computer system 303 also includes a memory 314 that holds data for computer system 303 or other components (or a combination of both) that may be connected to either or both of local area network 301 and wide area network 302. For example, memory 314 may be a database storing data consistent with this disclosure. Although illustrated as a single memory 314 in FIG. 3, two or more memories may be used according to particular needs, desires, or particular implementations of computer system 303 and the described functionality. While memory 314 is illustrated as an integral component of computer system 303, in alternative implementations, memory 314 may be external to computer system 303. In some embodiments, a table of pump data representing a pump curve for a pump is uploaded to memory 314 and accessible to uncompressible liquid quality determination application 316. In addition to holding data, the memory may be a non-transitory medium storing computer readable instruction capable of execution by computer processor 312 and having the functionality for carrying out manipulation of the data including mathematical computations.

Uncompressible liquid quality determination application 316 may be an algorithmic software engine providing functionality according to particular needs, desires, or particular implementations of computer system 303, particularly with respect to functionality described in this disclosure. For example, uncompressible liquid quality determination application 316 may include instructions executable by processors 312 to determine an uncompressible liquid quality value based upon real-time measurements similar to that discussed above in relation to FIGS. 2A-2B.

Location determination circuit and application 310 may be any location determination hardware or software known in the art including, but not limited to, a global navigation satellite system (GNSS) based location circuit. Based upon the disclosure provided herein, one of ordinary skill in the art will recognize a variety of location circuits and/or applications that may be used in relation to different embodiments. Location information generated from location determination circuit and application 310 may be transmitted along with an uncompressible liquid quality value to a recipient device via wide area network 302.

Time determination circuit and application 308 may be any time determination hardware or software known in the art including, but not limited to, a clock circuit. Based upon the disclosure provided herein, one of ordinary skill in the art will recognize a variety of time circuits and/or applications that may be used in relation to different embodiments. Time information generated from time determination circuit and application 308 may be transmitted along with an uncompressible liquid quality value to a recipient device via wide area network 302.

A display driver 318 may be any circuit or application configured to generate display information and to provide the display information to an attached or otherwise communicably coupled display device. Based upon the disclosure provided herein, one of ordinary skill in the art will recognize a variety of display drivers and corresponding display devices that may be used in relation to different embodiments. Display information generated by display driver 318 may include, but is not limited to, an uncompressible liquid quality value to be displayed locally.

Figure 4:
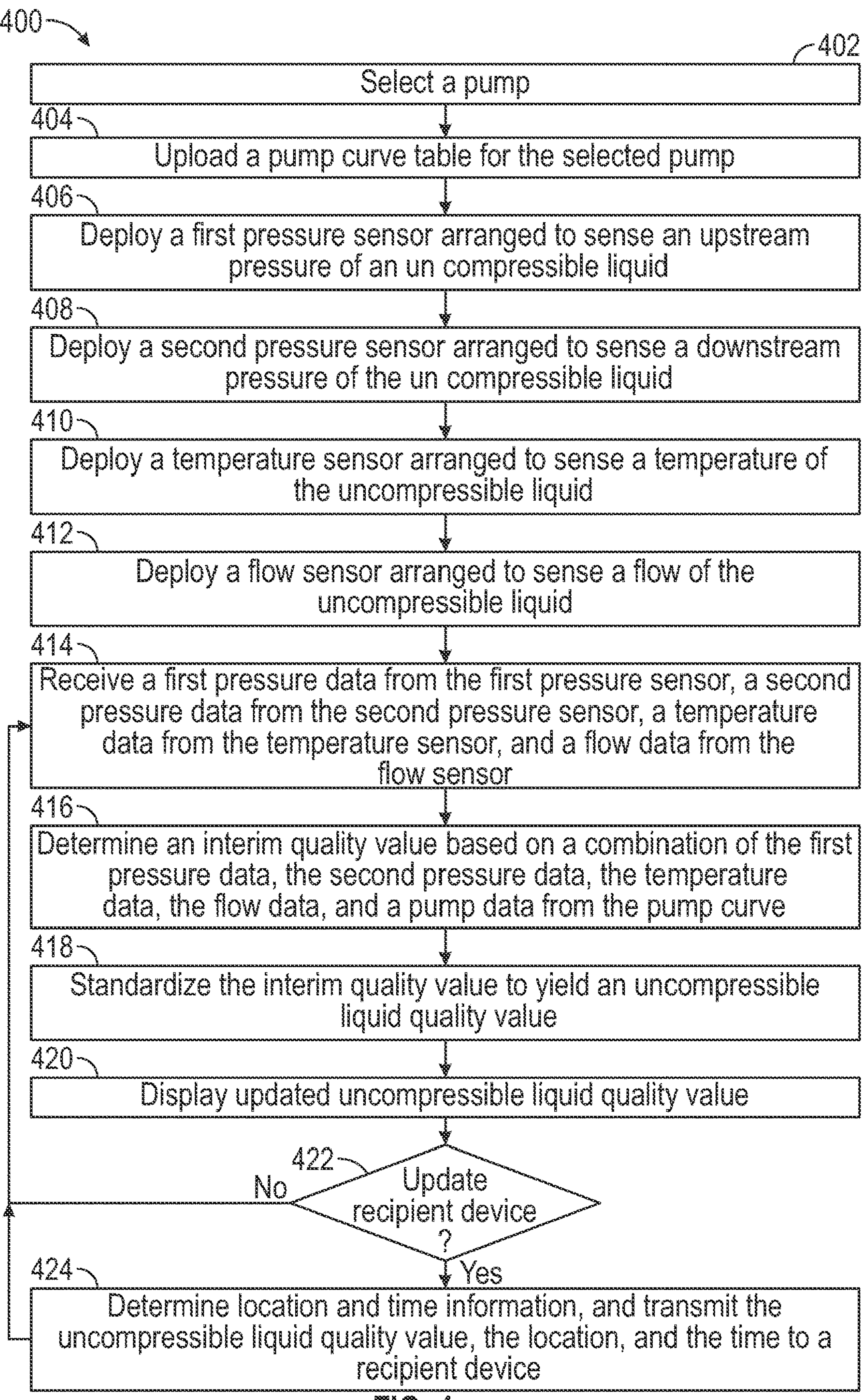
FIG. 4 is a flow diagram showing a method in accordance with some embodiments for determining an uncompressible liquid quality value using real-time measurements of an uncompressible liquid moving through a pump.

Turning to FIG. 4, a flow diagram 400 shows a method in accordance with some embodiments for determining an uncompressible liquid quality value using real-time measurements of an uncompressible liquid moving through a pump. Following flow diagram 400, a pump is selected (block 402). The selected pump may be a pump that is fixed in place at a location to be monitored. Selecting the pump may include, but is not limited to, providing identifying characteristics of the pump sufficient to identify data describing the pump operation. Such characteristics may include, but are not limited to, a manufacturer name, pump type, pump size, and/or pump model number. Based upon the disclosure provided herein, one of ordinary skill in the art will recognize a variety of identifying characteristics that may be provided in relation to different embodiments.

A pump curve for the selected pump is uploaded to an uncompressible liquid quality determination system (block 404). The pump curve may be represented as a table of values and may be maintained in a memory local to the uncompressible liquid quality determination system. In some embodiments, the table of values are a table of head to flow values that may be accessed using a measured flow.

A first pressure sensor is deployed upstream from the selected pump and configured to measure an upstream pressure (i.e., a suction pressure) near an inlet of the selected pump (block 406). Deploying the first pressure sensor may include permanently installing the first pressure sensor in a pipe leading to the inlet of the selected pump or may include removably installing the first pressure sensor in the pipe leading to the inlet of the selected pump. A second pressure sensor is deployed downstream from the selected pump and configured to measure a downstream pressure (i.e., a discharge pressure) near and an outlet of the selected pump (block 408). Deploying the second pressure sensor may include permanently installing the second pressure sensor in a pipe leading from the outlet of the selected pump or may include removably installing the second pressure sensor in the pipe leading from the outlet of the selected pump.

A temperature sensor is deployed in such a way as to sense a temperature of an uncompressible liquid (block 410), and a flow sensor is deployed in such a way as to sense a flow of the uncompressible liquid (block 412). The temperature sensor may be deployed either upstream or downstream from the pump. Similarly, the flow sensor may be deployed either upstream or downstream from the pump.

A first pressure data (e.g., a suction pressure ($P_s$)) is received from the first pressure sensor, a second pressure data (e.g., a discharge pressure ($P_d$)) is received from the second pressure sensor, a temperature (T) is received from the temperature sensor, and a flow (F) is received from the flow sensor (block 414). Each of the aforementioned data may be received in real-time. Such real-time data may be received immediately as the respective sensor indicates a change or within a known update rate for the particular sensor. In either case, the data is considered real-time data.

An interim quality value is determined based upon a combination of the first pressure data, the second pressure data, the temperature data, and the flow data (block 416). In some embodiments, this includes accessing the table of values representing the pump curve for the selected pump using the flow data. In particular, a head to flow value (H) corresponding to the measured flow data is accessed from the table of values. Using the pressure data and the head to flow value, specific gravity (SG) of the uncompressible liquid moving through the pump is calculated accordance with the following equation:

$$SG=(P_d-P_s)*2.31/H.$$

It is noted that the above-described specific gravity qualifies as an uncompressible liquid quality value as that phrase is defined herein. Next, the above-described specific gravity is temperature corrected to yield a temperature corrected specific gravity ($SG_{60}$) for a temperature of sixty (60) degrees Fahrenheit using the following equation:

$$SG_{60}=SG+[3.31*10^{-4}*(T(^{\circ}\text{ F.})-60)].$$

It is noted that the above-described temperature corrected specific gravity also qualifies as an uncompressible liquid quality value as that phrase is defined herein.

The interim quality value may then be standardized to yield an uncompressible liquid quality value (block 418). In some embodiments, this standardization includes converting the temperature corrected specific gravity to American Petroleum Institute (API) gravity using the following equation:

$$\text{API Gravity}=(141.5/SG_{60})-131.5.$$

It is noted that the above-described API gravity also qualifies as an uncompressible liquid quality value as that phrase is defined herein.

The updated uncompressible liquid quality value is displayed (block 420). This may include displaying the uncompressible liquid quality value as it changes due to changes in one or more of the first pressure data, the second pressure data, the temperature data, and/or the flow data. In some embodiments, a delay in updating is implemented to assure the information displayed is not changing so rapidly that it cannot be interpreted by an operator.

It is determined whether it is time to transmit the updated uncompressible liquid quality value to a recipient device (block 422). In some cases, the updated uncompressible liquid quality value is transmitted every five (5) minutes. Based upon the disclosure provided herein, one of ordinary skill in the art will recognize a variety of transmission rates that may be used in relation to different embodiments. Where it is time to transmit (block 422), the location of the device generating the updated uncompressible liquid quality value and a current time is determined, and the updated uncompressible liquid quality value, the time, and the location are transmitted to the recipient device (block 424). Whether it is time to transmit (block 422) or not, the processes of blocks 414-424 are repeated and updated uncompressible liquid quality value is changed whenever any of the first pressure data, the second pressure data, the temperature data, and/or the flow data change.

Figure 5:
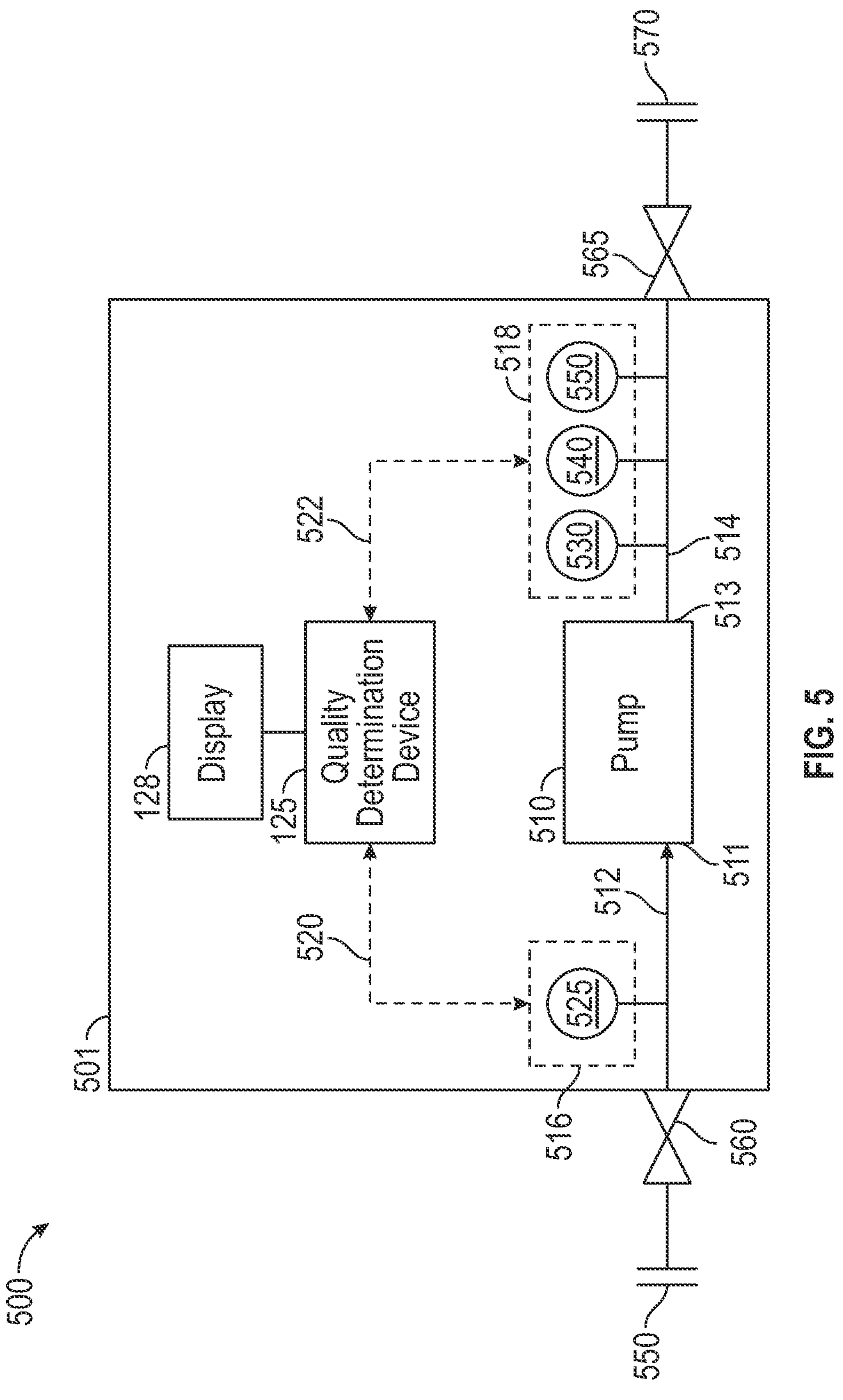
FIG. 5 shows an uncompressible liquid quality determination system including a pump and incorporated in a mobile container in accordance with various embodiments.

Turning to FIG. 5, an uncompressible liquid quality determination system 500 is shown including a pump 510 and incorporated in a mobile container 501 in accordance with various embodiments. Mobile container 501 may be any housing capable of holding pump 510, a sensor set 516, a sensor set 518, quality determination device 125, display 128, pipe 512, and pipe 514. In some embodiments, mobile container 501 is a skid or a container truck that is easily moved to a location where the quality of an uncompressible liquid is to be determined. Based upon the disclosure provided herein, one of ordinary skill in the art will recognize a variety of mobile containers that may be used in relation to different embodiments.

An inlet connector 550 may be connected to an uncompressible liquid source (not shown) and a valve 560 controls flow of an uncompressible liquid from the uncompressible liquid source into pipe 512. The uncompressible liquid source may be any source of uncompressible liquid including, but not limited to, a producing well or a storage tank. Based upon the disclosure provided herein, one of ordinary skill in the art will recognize a number of uncompressible liquid sources that may be used in relation to different embodiments. Inlet connector 550 may be any connector known in the art for connecting a pipe from a liquid source, and valve 560 may be any apparatus known in the art for selectable control of liquid flow. An outlet connector 570 may be connected to an uncompressible liquid destination (not shown) and a valve 565 controls flow of the uncompressible liquid from pipe 514 to the uncompressible liquid destination. The uncompressible liquid destination may be any destination for uncompressible liquid including, but not limited to, a storage tank or a distribution system. Based upon the disclosure provided herein, one of ordinary skill in the art will recognize a number of uncompressible liquid destinations that may be used in relation to different embodiments. Valve 565 may be any apparatus known in the art for selectable control of liquid flow.

Pump 510 may be engaged to pump the uncompressible liquid from the uncompressible liquid source through pipe 512 to a pump inlet 511 of pump 510, and through a pump outlet 513 and into pipe 514. As the uncompressible liquid flows through pipe 512, pump 510, and pipe 514, it is measured by sensor set 516 and sensor set 518. As shown, sensor set 516 includes a pressure sensor 525 measuring a suction pressure ($P_s$). Pressure sensor 525 may be any pressure sensor known in the art that is capable of measuring the suction pressure of pump 510. Further, pressure sensor 525 is located sufficiently close to pump inlet 511 to provide an accurate measurement of the suction pressure. Sensor set 518 includes: a pressure sensor 530 measuring a discharge pressure ($P_d$), a temperature sensor 540 measuring a temperature (T) of the uncompressible liquid, and a flow sensor 550 measuring a flow (F) of the uncompressible liquid. Pressure sensor 530 may be any pressure sensor known in the art that is capable of measuring the discharge pressure of pump 510. Further, pressure sensor 530 is located sufficiently close to pump outlet 513 to provide an accurate measurement of the discharge pressure. Temperature sensor 540 may be any temperature sensor known in the art that is capable of measuring the temperature of an uncompressible liquid flowing in a pipe. Flow sensor 550 may be any temperature sensor known in the art that is capable of measuring the flow of an uncompressible liquid flowing in a pipe. Temperature sensor 540 and flow sensor 550 are located sufficiently close to pump 510 to provide an accurate measurement of the temperature and flow of the uncompressible liquid at the pump. While temperature sensor 540 and flow sensor 550 are shown downstream from pump 510, in other embodiments one or both of temperature sensor 540 and flow sensor 550 may be upstream from pump 510.

Sensor set 516 transmits the suction pressure to quality determination device 125 via a communication link 520. Communication link 520 may be any communication link known in the art including, but not limited to, a wired communication link or a wireless communication link. Further, the suction pressure may be transmitted from sensor set 516 using any communication protocol known in the art. In one particular embodiment, communication link 520 is a hardwired communication link and the communication protocol is a universal serial bus (USB) protocol. Based upon the disclosure provided herein, one of ordinary skill in the art will recognize a variety of communication links and/or communication protocols that may be implemented between sensor set 516 and quality determination device 125.

Sensor set 518 transmits the discharge pressure, the temperature of the uncompressible liquid, and the flow of the uncompressible liquid via a communication link 522. In some embodiments, communication link 522 may include a communication link dedicated to each of the discharge pressure, the temperature, and the flow, respectively. In other embodiments, communication link 522 may include a single communication link that handles transmission of the discharge pressure, the temperature, and the flow. Communication link 522 may be any communication link known in the art including, but not limited to, a wired communication link or a wireless communication link. Further, each of the discharge pressure, the temperature, and the flow may be transmitted from sensor set 518 using any communication protocol known in the art. In one particular embodiment, communication link 522 is a hardwired communication link with a wired connection dedicated to each of pressure sensor 530, temperature sensor 540, and flow sensor 550; and the communication protocol is a USB protocol. Based upon the disclosure provided herein, one of ordinary skill in the art will recognize a variety of communication links and/or communication protocols that may be implemented between sensor set 518 and quality determination device 125.

In operation, quality determination device 125 receives the suction pressure from pressure sensor 525, the discharge pressure from pressure sensor 530, the temperature from temperature sensor 540, and the flow from flow sensor 550 in real-time. Quality determination device 125 accesses a head to flowrate (H) value from a table of values representing a pump curve of pump 110 using the received flow.

Quality determination device 125 calculates a specific gravity (SG) of the uncompressible liquid in accordance with the following equation:

$$SG=(P_d-P_s)*2.31/H.$$

In some embodiment, quality determination device 125 calculates a temperature corrected specific gravity ($SG_{60}$) for a temperature of sixty (60) degrees Fahrenheit using the following equation:

$$SG_{60}=SG+[3.31*10^{-4}*(T(°\text{ F.})-60)].$$

The temperature corrected specific gravity can be converted to American Petroleum Institute (API) gravity using the following equation:

$$\text{API Gravity}=(141.5/SG_{60})-131.5.$$

In the case of crude oil production, the calculated API gravity can be seen by a local operator on display 128 and used to compare with American Petroleum Institute (API) specifications. The comparison provides an onsite, real-time indication to the local operator as to the quality of the oil being produced and if the production is within a desired API range.

Figure 6:
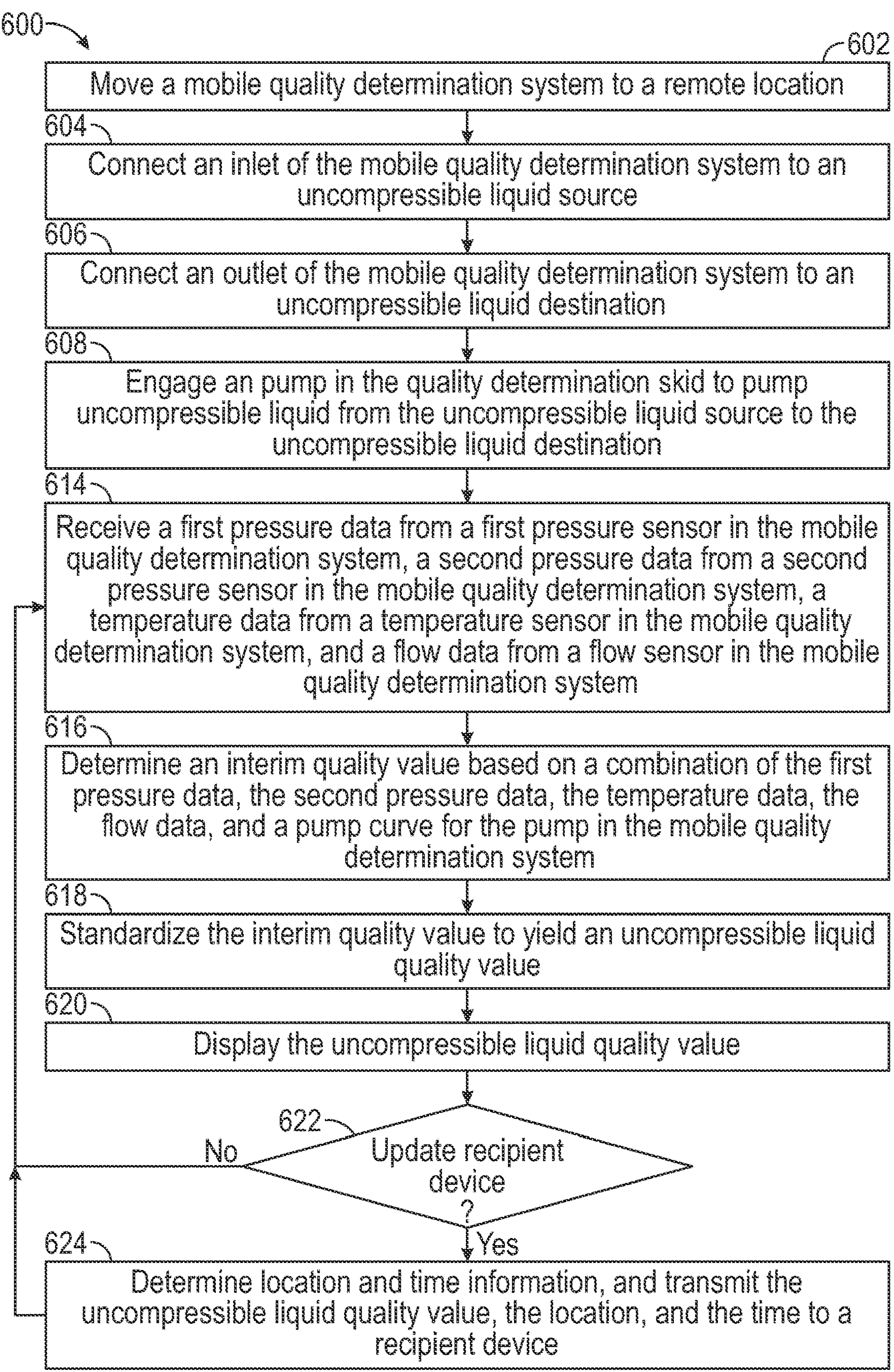
FIG. 6 is a flow diagram showing a method in accordance with some embodiments for using a mobile container housing an uncompressible liquid quality determination system to determine an uncompressible liquid quality value using real-time measurements of an uncompressible liquid moving through a pump.

Turning to FIG. 6, a flow diagram 600 shows a method in accordance with some embodiments for using a mobile container housing an uncompressible liquid quality determination system to determine an uncompressible liquid quality value using real-time measurements of an uncompressible liquid moving through a pump. Following flow diagram 600, a mobile quality determination system is moved to a remote location (block 602). In some embodiments the mobile quality determination system is implemented as a skid or a container truck. In such implementations, the skid or container truck is moved to the remote location.

An inlet of the mobile quality determination system is connected to an uncompressible liquid source (block 604) and an outlet of the mobile quality determination system is connected to an uncompressible liquid destination (block 606). Once connected, a pump included in the mobile quality determination system is engaged to begin pumping an uncompressible liquid from the uncompressible liquid source to the uncompressible liquid destination (block 608). This uncompressible liquid passes through pipes and the pump of the mobile quality determination system.

A first pressure data ($P_s$) is received from the first pressure sensor in the mobile quality determination system, a second pressure data ($P_d$) is received from the second pressure sensor in the mobile quality determination system, a temperature (T) is received from the temperature sensor in the mobile quality determination system, and a flow (F) is received from the flow sensor in the mobile quality determination system (block 614). Each of the aforementioned data may be received in real-time. Such real-time data may be received immediately as the respective sensor indicates a change or within a known update rate for the particular sensor. In either case, the data is considered real-time data.

An interim quality value is determined based upon a combination of the first pressure data, the second pressure data, the temperature data, the flow data (block 616). In some embodiments, this includes accessing a table of values representing the pump curve for the pump included in the mobile quality determination system. The table of values is accessed using the flow data. In particular, a head to flow value (H) corresponding to the measured flow data is accessed from the table of values. Using the pressure data and the head to flow value, specific gravity (SG) of the uncompressible liquid moving through the pump is calculated accordance with the following equation:

$$SG=(P_d-P_s)*2.31/H.$$

It is noted that the above-described specific gravity qualifies as an uncompressible liquid quality value as that phrase is defined herein. Next, the above-described specific gravity is temperature corrected to yield a temperature corrected specific gravity ($SG_{60}$) for a temperature of sixty (60) degrees Fahrenheit using the following equation:

$$SG_{60}=SG+[3.31*10^{-4}*(T(°\text{ F.})-60)].$$

It is noted that the above-described temperature corrected specific gravity also qualifies as an uncompressible liquid quality value as that phrase is defined herein.

The interim quality value may then be standardized to yield an uncompressible liquid quality value (block 618). In some embodiments, this standardization includes converting the temperature corrected specific gravity to American Petroleum Institute (API) gravity using the following equation:

$$\text{API Gravity}=(141.5/SG_{60})-131.5.$$

It is noted that the above-described API gravity also qualifies as an uncompressible liquid quality value as that phrase is defined herein.

The updated uncompressible liquid quality value is displayed (block 620). This may include displaying the uncompressible liquid quality value as it changes due to changes in one or more of the first pressure data, the second pressure data, the temperature data, and/or the flow data. In some embodiments, a delay in updating is implemented to assure the information displayed is not changing so rapidly that it cannot be interpreted by an operator.

It is determined whether it is time to transmit the updated uncompressible liquid quality value to a recipient device (block 622). In some cases, the updated uncompressible liquid quality value is transmitted every five (5) minutes. Based upon the disclosure provided herein, one of ordinary skill in the art will recognize a variety of transmission rates that may be used in relation to different embodiments. Where it is time to transmit (block 622), the location of the device generating the updated uncompressible liquid quality value and a current time is determined, and the updated uncompressible liquid quality value, the time, and the location are transmitted to the recipient device (block 424). Whether it is time to transmit (block 622) or not, the processes of blocks 614-624 are repeated and updated uncompressible liquid quality value is changed whenever any of the first pressure data, the second pressure data, the temperature data, and/or the flow data change.

Figure 7:
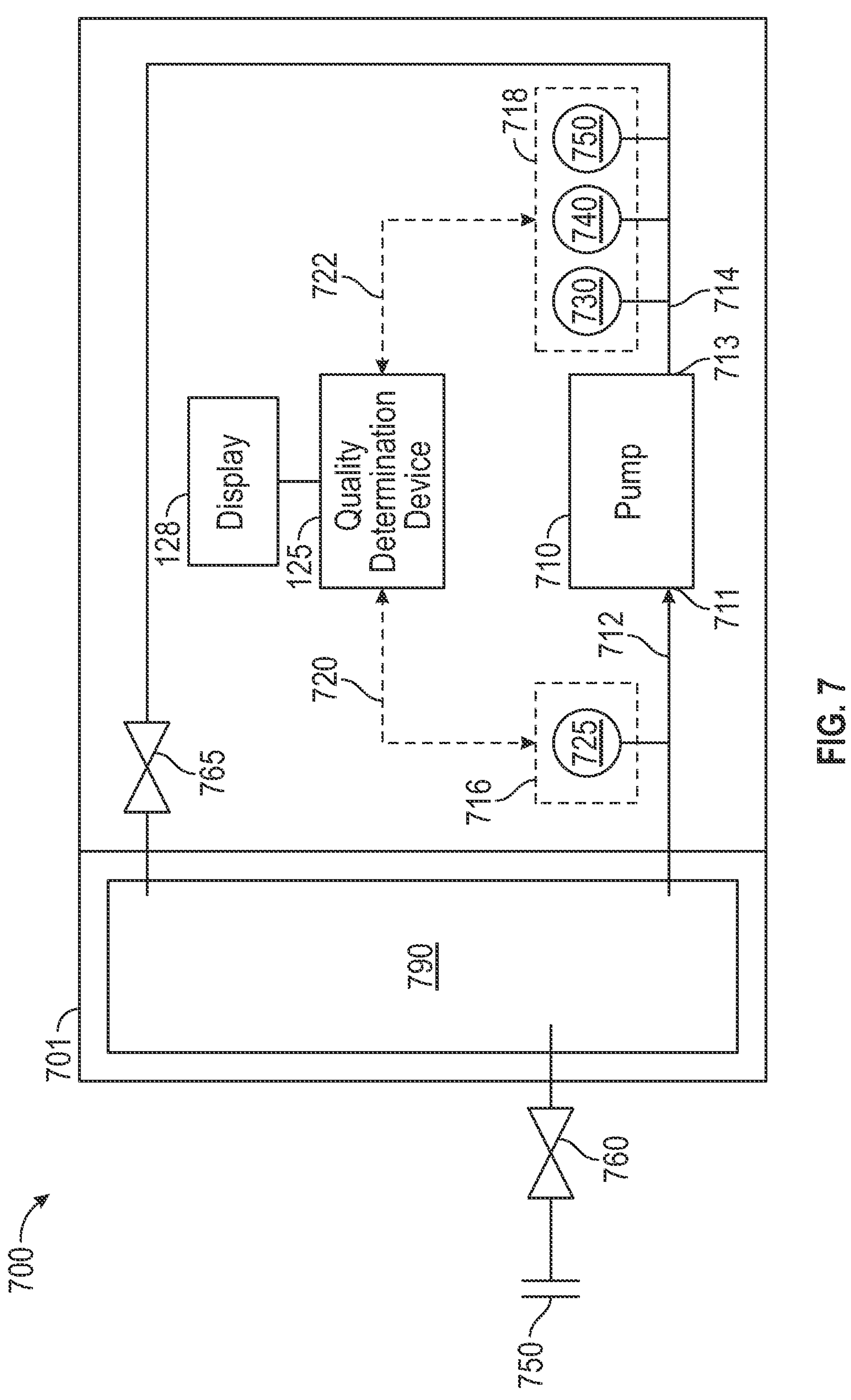
FIG. 7 shows an uncompressible liquid quality determination system including a pump and a tank incorporated in a container in accordance with some embodiments.

Turning to FIG. 7, an uncompressible liquid quality determination system 700 is shown including a pump 710 and a tank 790. Uncompressible liquid quality determination system 700 includes the components including tank 790 and pump 710 incorporated in a container 701 in accordance with various embodiments. Container 701 may be any housing capable of holding pump 710, a sensor set 716, a sensor set 718, quality determination device 125, display 128, pipe 712, pipe 714, and a valve 765. In some embodiments, container 701 is a mobile container such as, for example, a skid or a container truck that is easily to a location where the quality of an uncompressible liquid is to be determined. In other embodiments, container 701 is a fixed location container. Based upon the disclosure provided herein, one of ordinary skill in the art will recognize a variety of containers that may be used in relation to different embodiments.

An inlet connector 750 may be connected to an uncompressible liquid source (not shown) and a valve 760 controls flow of an uncompressible liquid from the uncompressible liquid source into tank 790. In some cases, the uncompressible liquid source is a tanker truck from which the uncompressible liquid may be pumped. Inlet connector 750 may be any connector known in the art for connecting a pipe from a liquid source, and valve 760 may be any apparatus known in the art for selectable control of liquid flow.

A valve 765 controls flow of the uncompressible liquid from tank 790, through pipe 712, pump 710 via a pump inlet 711 and a pump outlet 713, through pipe 714, and back into tank 790. Valve 765 may be any apparatus known in the art for selectable control of liquid flow.

Once tanked 790 is filled via valve 760, valve 760 may be closed. Pump 710 may be engaged to pump the uncompressible liquid from tank 790 through pipe 712 to pump inlet 711 of pump 710, through pump outlet 713, and into pipe 714. The uncompressible liquid is returned to tank 790 via valve 765. As the uncompressible liquid flows through pipe 712, pump 710, and pipe 714, it is measured by sensor set 716 and sensor set 718. As shown, sensor set 716 includes a pressure sensor 725 measuring a suction pressure ($P_s$). Pressure sensor 725 may be any pressure sensor known in the art that is capable of measuring the suction pressure of pump 710. Further, pressure sensor 725 is located sufficiently close to pump inlet 711 to provide an accurate measurement of the suction pressure. Sensor set 718 includes: a pressure sensor 730 measuring a discharge pressure ($P_d$), a temperature sensor 740 measuring a temperature (T) of the uncompressible liquid, and a flow sensor 750 measuring a flow (F) of the uncompressible liquid. Pressure sensor 730 may be any pressure sensor known in the art that is capable of measuring the discharge pressure of pump 710. Further, pressure sensor 730 is located sufficiently close to pump outlet 713 to provide an accurate measurement of the discharge pressure. Temperature sensor 740 may be any temperature sensor known in the art that is capable of measuring the temperature of an uncompressible liquid flowing in a pipe. Flow sensor 750 may be any temperature sensor known in the art that is capable of measuring the flow of an uncompressible liquid flowing in a pipe. Temperature sensor 740 and flow sensor 750 are located sufficiently close to pump 710 to provide an accurate measurement of the temperature and flow of the uncompressible liquid at the pump. While temperature sensor 740 and flow sensor 750 are shown downstream from pump 710, in other embodiments one or both of temperature sensor 740 and flow sensor 750 may be upstream from pump 710.

Sensor set 716 transmits the suction pressure to quality determination device 125 via a communication link 720. Communication link 720 may be any communication link known in the art including, but not limited to, a wired communication link or a wireless communication link. Further, the suction pressure may be transmitted from sensor set 716 using any communication protocol known in the art. In one particular embodiment, communication link 720 is a hardwired communication link and the communication protocol is a universal serial bus (USB) protocol. Based upon the disclosure provided herein, one of ordinary skill in the art will recognize a variety of communication links and/or communication protocols that may be implemented between sensor set 716 and quality determination device 125.

Sensor set 718 transmits the discharge pressure, the temperature of the uncompressible liquid, and the flow of the uncompressible liquid via a communication link 722. In some embodiments, communication link 722 may include a communication link dedicated to each of the discharge pressure, the temperature, and the flow, respectively. In other embodiments, communication link 722 may include a single communication link that handles transmission of the discharge pressure, the temperature, and the flow. Communication link 722 may be any communication link known in the art including, but not limited to, a wired communication link or a wireless communication link. Further, each of the discharge pressure, the temperature, and the flow may be transmitted from sensor set 718 using any communication protocol known in the art. In one particular embodiment, communication link 722 is a hardwired communication link with a wired connection dedicated to each of pressure sensor 730, temperature sensor 740, and flow sensor 750; and the communication protocol is a USB protocol. Based upon the disclosure provided herein, one of ordinary skill in the art will recognize a variety of communication links and/or communication protocols that may be implemented between sensor set 718 and quality determination device 125.

In operation, quality determination device 125 receives the suction pressure from pressure sensor 725, the discharge pressure from pressure sensor 730, the temperature from temperature sensor 740, and the flow from flow sensor 750 in real-time. Quality determination device 125 accesses a head to flowrate (H) value from a table of values representing a pump curve of pump 110 using the received flow.

Quality determination device 125 calculates a specific gravity (SG) of the uncompressible liquid in accordance with the following equation:

$$SG=(P_d-P_s)*2.31/H.$$

In some embodiment, quality determination device 125 calculates a temperature corrected specific gravity ($SG_{60}$) for a temperature of sixty (60) degrees Fahrenheit using the following equation:

$$SG_{60}=SG+[3.31*10^{-4}*(T(° \text{F.})-60)].$$

The temperature corrected specific gravity can be converted to American Petroleum Institute (API) gravity using the following equation:

$$\text{API Gravity}=(141.5/SG_{60})-131.5.$$

In the case of crude oil production, the calculated API gravity can be seen by a local operator on display 128 and used to compare with American Petroleum Institute (API) specifications. The comparison provides an onsite, real-time indication to the local operator as to the quality of the oil being produced and if the production is within a desired API range.

Figure 8:
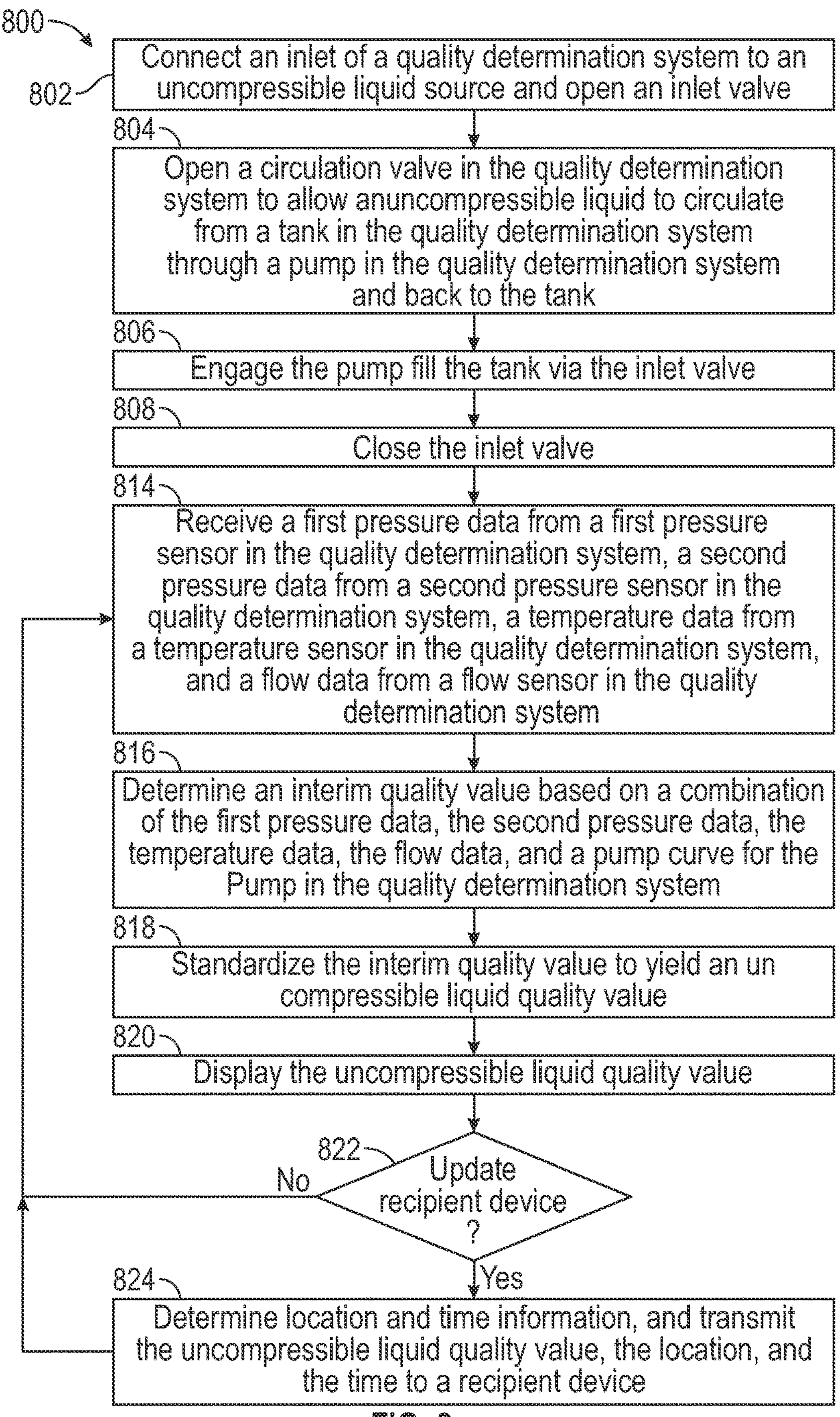
FIG. 8 is a flow diagram showing a method in accordance with some embodiments for determining an uncompressible liquid quality value using real-time measurements of an uncompressible liquid drawn from a tank and moving through a pump where the pump and the tank are both incorporated in a container.

Turning to FIG. 8, a flow diagram 800 shows a method in accordance with some embodiments for determining an uncompressible liquid quality value using real-time measurements of an uncompressible liquid drawn from a tank and moving through a pump where the pump and the tank are tank are both incorporated in a container housing a quality determination system. The container may be mobile or fixed in location. In some embodiments, the tank is a very large oil tank included as part of an oil storage facility and the container is attached to the side of the tank via pipes that move oil from the tank through a pump included in the container.

Following flow diagram 800, an inlet of a quality determination system is connected to an uncompressible liquid source (block 802). An inlet valve is opened to allow uncompressible liquid from the uncompressible liquid source to enter the tank. A circulation valve of the quality determination system is opened to allow an uncompressible liquid to circulate from the tank through the pump of the quality determination system and back to the tank (block 804). The pump of the quality determination system is engaged to pump the uncompressible liquid from the tank, through the pump and the circulation valve, and back to the tank (block 806). Where applicable, the inlet valve is closed such that additional uncompressible liquid form the uncompressible liquid source is not admitted into the tank (block 808).

A first pressure data ($P_s$) is received from the first pressure sensor in the quality determination system, a second pressure data ($P_d$) is received from the second pressure sensor in the quality determination system, a temperature (T) is received from the temperature sensor in the quality determination system, and a flow (F) is received from the flow sensor in the quality determination system (block 814). Each of the aforementioned data may be received in real-time. Such real-time data may be received immediately as the respective sensor indicates a change or within a known update rate for the particular sensor. In either case, the data is considered real-time data.

An interim quality value is determined based upon a combination of the first pressure data, the second pressure data, the temperature data, the flow data (block 816). In some embodiments, this includes accessing a table of values representing the pump curve for the pump included in the quality determination system. The table of values is accessed using the flow data. In particular, a head to flow value (H) corresponding to the measured flow data is accessed from the table of values. Using the pressure data and the head to flow value, specific gravity (SG) of the uncompressible liquid moving through the pump is calculated accordance with the following equation:

$$SG=(P_d-P_s)*2.31/H.$$

It is noted that the above-described specific gravity qualifies as an uncompressible liquid quality value as that phrase is defined herein. Next, the above-described specific gravity is temperature corrected to yield a temperature corrected specific gravity ($SG_{60}$) for a temperature of sixty (60) degrees Fahrenheit using the following equation:

$$SG_{60}=SG+[3.31*10^{-4}*(T(° F.)-80)].$$

It is noted that the above-described temperature corrected specific gravity also qualifies as an uncompressible liquid quality value as that phrase is defined herein.

The interim quality value may then be standardized to yield an uncompressible liquid quality value (block 818). In some embodiments, this standardization includes converting the temperature corrected specific gravity to American Petroleum Institute (API) gravity using the following equation:

$$\text{API Gravity}=(141.5/SG_{60})-131.5.$$

It is noted that the above-described API gravity also qualifies as an uncompressible liquid quality value as that phrase is defined herein.

The updated uncompressible liquid quality value is displayed (block 820). This may include displaying the uncompressible liquid quality value as it changes due to changes in one or more of the first pressure data, the second pressure data, the temperature data, and/or the flow data. In some embodiments, a delay in updating is implemented to assure the information displayed is not changing so rapidly that it cannot be interpreted by an operator.

It is determined whether it is time to transmit the updated uncompressible liquid quality value to a recipient device (block 822). In some cases, the updated uncompressible liquid quality value is transmitted every five (5) minutes. Based upon the disclosure provided herein, one of ordinary skill in the art will recognize a variety of transmission rates that may be used in relation to different embodiments. Where it is time to transmit (block 822), the location of the device generating the updated uncompressible liquid quality value and a current time is determined, and the updated uncompressible liquid quality value, the time, and the location are transmitted to the recipient device (block 424). Whether it is time to transmit (block 822) or not, the processes of blocks 814-624 are repeated and updated uncompressible liquid quality value is changed whenever any of the first pressure data, the second pressure data, the temperature data, and/or the flow data change.

Figure 9:
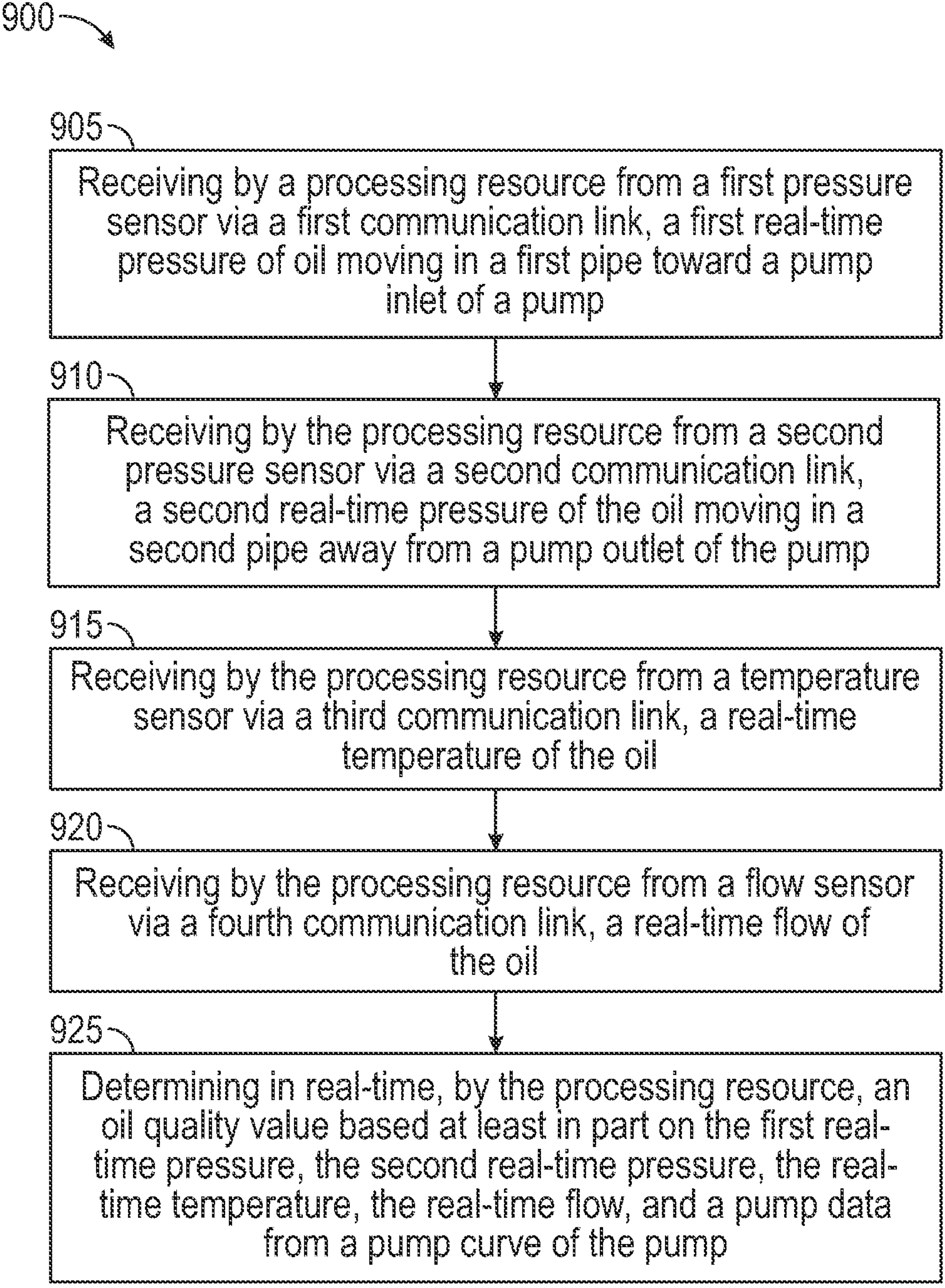
FIG. 9 is a flow diagram showing a method in accordance with some embodiments for determining an uncompressible liquid quality value using real-time measurements of an uncompressible liquid moving through a pump.

Turning to FIG. 9, a flow diagram 900 shows a method in accordance with some embodiments for determining an uncompressible liquid quality value using real-time measurements of an uncompressible liquid moving through a pump. Following flow diagram 900, a first real-time pressure of oil moving in a first pipe toward a pump inlet of a pump is received by a processing resource from a first pressure sensor via a first communication link (block 905). A second real-time pressure of the oil moving in a second pipe away from a pump outlet of the pump is received by the processing resource from a second pressure sensor via a second communication link (block 910). A real-time temperature of the oil is received by the processing resource from a temperature sensor via a third communication link (block 915). A flow of the oil is received by the processing resource from a flow sensor via a fourth communication link (block 920). An oil quality value is determined based at least in part on the first real-time pressure, the second real-time pressure, the real-time temperature, the real-time flow, and a pump data from a pump curve of the pump (block 925).

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims.

What is claimed is:

1. A system, the system comprising:

a first pressure sensor deployed upstream from a pump and configured to sense a first pressure of an uncompressible liquid moving in a first pipe toward the pump;

a second pressure sensor deployed downstream from the pump and configured to sense a second pressure of the uncompressible liquid moving in a second pipe away from the pump;

a flow sensor configured to sense a flow of the uncompressible liquid; and a quality determination device configured to:

receive the first pressure from the first pressure sensor;

receive the second pressure from the second pressure sensor;

determine in real-time an uncompressible liquid quality value based at least in part on the first pressure, the second pressure, and a pump data from a pump curve of the pump; and select the pump data from the pump curve based upon the flow.

2. The system of claim 1, wherein determining in real-time the uncompressible liquid quality value comprises:

calculating a pressure difference between the first pressure and the second pressure;

multiplying the pressure difference by a predetermined value to yield a product; and dividing the product by the pump data to yield the uncompressible liquid quality value.

3. The system of claim 1, wherein determining in real-time the uncompressible liquid quality value comprises:

calculating a pressure difference between the first pressure and the second pressure;

multiplying the pressure difference by a predetermined value to yield a product;

selecting the pump data from the pump curve based upon the flow; and dividing the product by the pump data to yield the uncompressible liquid quality value.

4. The system of claim 1, the system further comprising:

a temperature sensor configured to sense a temperature of the uncompressible liquid.

5. The system of claim 4, wherein determining in real-time the uncompressible liquid quality value comprises:

calculating a pressure difference between the first pressure and the second pressure;

multiplying the pressure difference by a predetermined value to yield a product;

selecting the pump data from the pump curve based upon the flow;

dividing the product by the pump data to yield an interim quality value; and using the temperature to convert the interim quality value to the uncompressible liquid quality value.

6. The system of claim 4, wherein the first pressure sensor, the second pressure sensor, the flow sensor, and the temperature sensor are each communicably coupled to the quality determination device via at least one wireless communication link.

7. The system of claim 1, the system further comprising:

the pump having a pump inlet and a pump outlet;

an inlet connector;

an outlet connector;

the first pipe;

the second pipe; and a mobile container housing at least: the pump, the first pipe coupled between the pump inlet and the inlet connector, the second pipe coupled between the pump outlet and the outlet connector, the first pressure sensor, and the second pressure sensor;

wherein the inlet connector is configured for connection to an uncompressible liquid source; and wherein the outlet connector is configured for connection to an uncompressible liquid destination.

8. The system of claim 7, wherein the uncompressible liquid destination comprises a tank, and wherein the uncompressible liquid source comprises the tank.

9. The system of claim 1, the system further comprising:

the pump having a pump inlet and a pump outlet;

an inlet connector;

the first pipe;

the second pipe;

a circulation valve;

a tank;

a container housing at least: the tank, the inlet connector coupled to the tank, the pump, the first pipe coupled between the pump inlet and the tank, the second pipe coupled between the pump outlet and the circulation valve, the circulation valve coupled between the second pipe and the tank, the first pressure sensor, and the second pressure sensor;

wherein the inlet connector is configured to allow an uncompressible liquid from an uncompressible liquid source to enter the tank; and wherein the circulation valve control circulation of the uncompressible liquid from the tank to the pump via the first pipe, and from the pump to the tank via the second pipe.

10. The system of claim 1, the system further comprising:

a display, wherein the quality determination device is further configured to display the uncompressible liquid quality value via the display.

11. The system of claim 1, wherein the quality determination device comprises a transmitter, and wherein the quality determination device is further configured to transmit the uncompressible liquid quality value to a recipient device via the transmitter.

12. The system of claim 1, wherein the quality determination device is a handheld, mobile quality determination device comprising an integrated display, and wherein the handheld, mobile quality determination device is configured to display the uncompressible liquid quality value via the integrated display.

13. The system of claim 1, wherein the pump is a centrifugal pump.

14. The system of claim 1, wherein the uncompressible liquid is crude oil.

15. A method for real-time oil quality determination, comprising:

receiving by a processing resource from a first pressure sensor via a first communication link, a first real-time pressure of oil moving in a first pipe toward a pump inlet of a pump;

receiving by the processing resource from a second pressure sensor via a second communication link, a second real-time pressure of the oil moving in a second pipe away from a pump outlet of the pump;

receiving by the processing resource from a temperature sensor via a third communication link, a real-time temperature of the oil;

receiving by the processing resource from a flow sensor via a fourth communication link, a flow of the oil;

determining in real-time, by the processing resource, an oil quality value based at least in part on the first real-time pressure, the second real-time pressure, the real-time temperature, the real-time flow, and a pump data from a pump curve of the pump.

16. The method of claim 15, wherein two or more of the first communication link, the second communication link, the third communication link, and the fourth communication link are the same communication link.

17. The method of claim 15, wherein at least one of the first communication link, the second communication link, the third communication link, and the fourth communication link comprises a wireless communication link.

18. The method of claim 15, the method further comprising:

deploying a mobile container to a measurement location, wherein the mobile container houses at least:
the pump;
the first pipe coupled between the pump inlet and an inlet connector;
the second pipe coupled between the pump outlet and an outlet connector;
the first pressure sensor;
the second pressure sensor;
the temperature sensor; and
the flow sensor;
coupling the inlet connector to an oil source; and
coupling the outlet connector to an oil destination.

19. The method of claim 15, the system further comprising:

providing a container, wherein the container houses at least:
a tank;
an inlet connector coupled to the tank;
the pump;
the first pipe coupled between the pump inlet and the tank;
the second pipe coupled between the pump outlet and a circulation valve;
the circulation valve coupled between the second pipe and the tank;
the first pressure sensor;
the second pressure sensor;
the temperature sensor; and
the flow sensor;
filling the tank with the oil via the inlet connector; and
opening the circulation valve to allow the pump to circulate the oil from the tank through the first pipe and the second pipe.

* * * * *